(12) United States Patent
Jhon et al.

(10) Patent No.: US 10,630,045 B1
(45) Date of Patent: Apr. 21, 2020

(54) SINGLE PULSE LASER APPARATUS USING DOUBLE TRIGGER

(71) Applicant: KOREA INSTITUTE OF SCIENCE AND TECHNOLOGY, Seoul (KR)

(72) Inventors: Young Min Jhon, Seoul (KR); Hui Dong Yang, Seoul (KR); Byunghyuck Moon, Seoul (KR); Minah Seo, Seoul (KR); Chulki Kim, Seoul (KR); Taikjin Lee, Seoul (KR); Yongsang Ryu, Seoul (KR); Hyunseok Song, Seoul (KR); Jaehun Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 16/280,238

(22) Filed: Feb. 20, 2019

(30) Foreign Application Priority Data

Nov. 21, 2018 (KR) ........................ 10-2018-0144474

(51) Int. Cl.
*H01S 3/11* (2006.01)
*A61B 18/20* (2006.01)
*H01S 3/115* (2006.01)
*H01S 3/117* (2006.01)
*A61B 18/00* (2006.01)

(52) U.S. Cl.
CPC .......... *H01S 3/1109* (2013.01); *A61B 18/203* (2013.01); *H01S 3/1103* (2013.01); *H01S 3/115* (2013.01); *H01S 3/117* (2013.01); *A61B 2018/0047* (2013.01)

(58) Field of Classification Search
CPC ........ H01S 3/1109; H01S 3/117; H01S 3/115; H01S 3/1103; A61B 18/203; A61B 2018/0047
See application file for complete search history.

(56) References Cited

U.S. PATENT DOCUMENTS

| 7,929,579 B2 | 4/2011 | Hohm et al. |
| 2011/0155916 A1* | 6/2011 | Furusawa ........... H01S 3/06791 250/363.04 |
| 2016/0352068 A1* | 12/2016 | Jhon ..................... H01S 3/1109 |

OTHER PUBLICATIONS

Hee Dong Yang et al., "Cavity-Dumped Mode-Locked Picosecond Alexandrite Single Pulse Laser with Double Trigger System", The 23rd OptoElectronics and Communications Conference (OECC 2018) Technical Digest, Jul. 2-6, 2018, Jeju, Korea.

* cited by examiner

*Primary Examiner* — Xinning(Tom) Niu
(74) *Attorney, Agent, or Firm* — Rabin & Berdo, P.C.

(57) ABSTRACT

The present disclosure discloses a double trigger type single pulse laser apparatus configured to suppress additional pulses to increase single pulse energy and improve stability of output as compared to a conventional single trigger type single pulse laser apparatus. According to the present invention, there is provided a single pulse laser apparatus including a resonator which has a first mirror, a second mirror, a gain medium, an electro-optic modulator and an acousto-optic modulator configured to respectively perform Q-switching and mode-locking, the single pulse laser apparatus including a first photodiode configured to measure a laser beam oscillated by the resonator.

10 Claims, 3 Drawing Sheets

SINGLE PULSE LASER APPARATUS USING DOUBLE TRIGGER

SPECIFIC REFERENCE TO A GRACE PERIOD INVENTOR DISCLOSURE

This invention has been published in the thesis "The 23$^{rd}$ OptoElectronics and Communications Conference (OECC 2018) Technical Digest, Jul. 2-6, 2018, Jeju, Korea" on Jul. 5, 2018.

CROSS-REFERENCE TO RELATED APPLICATION

This application claims priority to and the benefit of Korean Patent Application No. 2018-0144474, filed on Nov. 21, 2018, the disclosure of which is incorporated herein by reference in its entirety.

BACKGROUND

1. Field of the Invention

The present invention relates to a laser apparatus and, more particularly, to a single pulse laser apparatus capable of increasing single pulse energy and improving output stability through a double trigger.

2. Discussion of Related Art

Recently, treatment techniques using lasers are being widely used. Treatment apparatuses using the lasers are used in dermatology hospitals, ophthalmology hospitals, and dental hospitals, for surgical operations, and the like. Among them, a laser treatment apparatus used in the dermatology hospital is generally used to treat lesions such as skin diseases or vascular diseases occurring on the skin, and a laser beam with a predetermined wavelength and intensity is emitted to the skin to achieve a treatment purpose. Various types of lasers are used for treatment in the dermatology hospital. An alexandrite laser (operating at 755 nm, developed in 2012) is primarily used to treat naturally occurring dermatologic pigmentation and tattooing and uses picosecond pulses to maximize a treatment effect while minimizing sequelae. In addition, a long pulse ruby laser is used to remove hair, and an Nd:YAG laser (operating at 1060 nm), a carbon dioxide $CO_2$ laser (operating at 10.6 micrometers), and an argon laser (operating at 488 to 514 nm) are used to treat dilated blood vessels.

Specifically, in the dermatology hospital, laser treatment apparatuses are used to treat a variety of dermal pathological problems such as skin discoloration, a dilated blood vessel, and a pigmentary disorder including a tattoo. The laser treatment apparatus can locally heat skin to increase a temperature of the skin to an extent to which proteins forming the skin are denatured or pigment particles are dispersed. In this case, unlike other research and industrial lasers, a pulse width and energy of a laser beam suitable for treating the wound skin are important. Particularly, in order to maximize a treatment effect, energy should be maximally concentrated at an output pulse, and to this end, a laser capable of outputting a single pulse is required.

Conventional techniques use a pulse picker method and a cavity dumping method to output a single picosecond pulse and high energy. However, when these methods are used, since a high speed and high voltage circuit is required, there is a problem in that burdens of circuit design, production costs, and power consumption occur, and since output energy is small, there is a problem in that an amplifier is used. Accordingly, a volume increases due to the use of the amplifier, burdens of power consumption and price occur due to a high voltage supplied to the amplifier.

U.S. Pat. No. 7,929,579 discloses a method of outputting a high energy single pulse by using one electro-optic modulator (EOM) and a cavity dumping method. However, in this case, since the high voltage EOM should be used, and a high speed and high voltage driving circuit is required, burdens of price and power consumption occur, and since both mode-locking and Q-switching should be performed using one EOM, there is a problem in that a burden of power consumption occurs due to a high voltage. In addition, a high speed and high voltage switching circuit should be fabricated to perform the mode-locking and Q-switching using the high voltage EOM. In addition, since high energy picosecond single pulse can be output, an amplifier is not required, but there is a limitation of generating one shot pulse because mode-locking is not completely performed.

PRIOR ART DOCUMENT

Patent Document (Patent document 0001) U.S. Pat. No. 7,929,579

SUMMARY OF THE INVENTION

The present invention is directed to providing a single pulse laser apparatus with increased output stability and single pulse energy as compared to a conventional single pulse laser apparatus.

The present disclosure is not limited to the above-described objectives, and other objectives which are not described above may be clearly understood by those skilled in the art from the following description.

According to an aspect of the present invention, there is provided a single pulse laser apparatus including a resonator which has a first mirror, a second mirror, a gain medium, an electro-optic modulator and an acousto-optic modulator configured to respectively perform Q-switching and mode-locking, the single pulse laser apparatus including a first photodiode configured to measure a laser beam oscillated by the resonator; a first synchronizer configured to convert an electrical signal output from the first photodiode to a transistor-transistor-logic (TTL) signal; a first delay unit configured to set a delay time which is determined in order to synchronize a mode-locked and Q-switched pulses with the TTL signal output from the first synchronizer, and output a first trigger TTL signal according to the delay time; a second synchronizer configured to convert an electrical signal output from the second photodiode to a TTL signal; a second delay unit configured to set a delay time which is determined in order to synchronize Q-switched pulses and a cavity dumping timing with the TTL signal output from the second synchronizer, and output a second trigger TTL signal according to the delay time; and a Q-driver configured to input the first TTL signal and the second trigger TTL signal to the electro-optic modulator configured to perform the Q-switching to operate the electro-optic modulator.

The first photodiode may be positioned at a region adjacent to the first mirror in the resonator, and the second photodiode may be positioned at a region adjacent to the acousto-optic modulator in the resonator.

The single pulse laser apparatus may further include a controller configured to monitor a pulse width and pulse energy of the laser beam output by the resonator, and determine the delay time.

In this case the controller may determine a duration time for which the trigger TTL signal lasts.

The single pulse laser apparatus may further include a power supply configured to supply energy to the gain medium and to input a synchronization TTL signal output when a lamp is pumped to the first delay unit and the second delay unit.

The acousto-optic modulator configured to perform the mode-locking may prelase laser beams having specific picosecond pulse widths In this case, the controller may determine the delay time on the basis of a relationship between an interval of the prelased pulses and a pulse width of the Q-switched pulse.

The single pulse laser apparatus may further include an etalon configured to adjust a pulse width of the laser beam in a range of 100 ps to 1 ns.

In this case, the etalon is formed as parallel flat plates having a predetermined reflectivity, is an optical element formed by depositing a multilayered dielectric thin film one side or both sides of the parallel flat plates formed of glass or quartz to increase the reflectivity, and limits a transmission wavelength band when the laser beam passes through the etalon so that the pulse width of the laser beam is adjusted due to the reflectivity, a thickness, and a refractive index of the etalon.

In this case, the etalon may include one or more etalons, and the etalons having different characteristics may be selectively used inside or outside the resonator to adjust the pulse width of the laser beam.

Other specific details of the present invention are contained in the detailed description and drawings.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
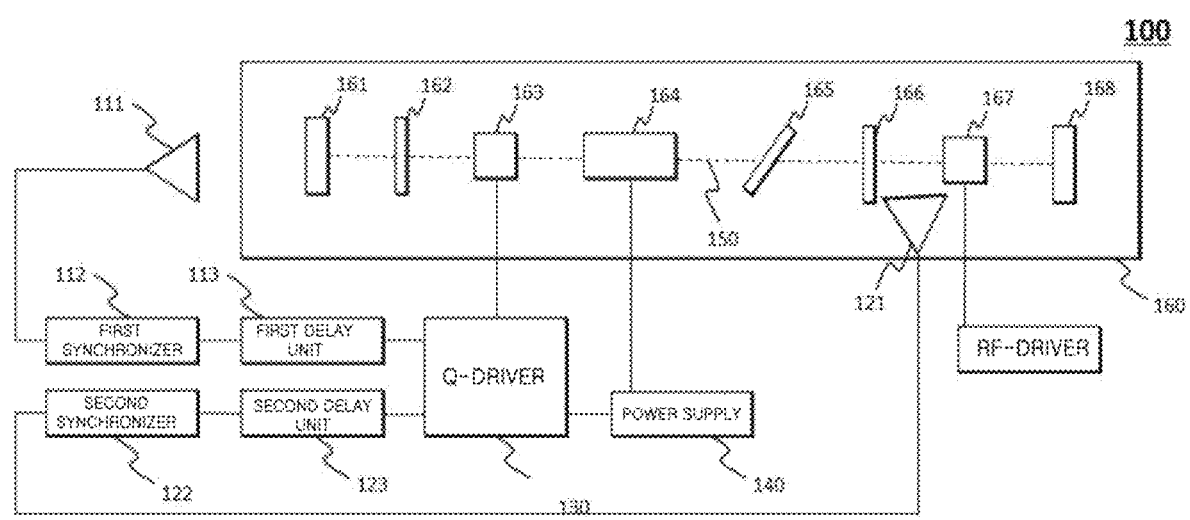
FIG. 1 is a block diagram illustrating a single pulse laser apparatus according to one embodiment of the present disclosure.

Advantages and features and methods of achieving the same of the present invention disclosed in the specification will be clearly understood with reference to the following detailed examples. However, the present invention is not limited to the examples to be disclosed below but may be implemented in various different forms. The examples are provided in order to fully explain the present invention and fully explain the scope of the present invention for those skilled in the art. The scope of the present invention is defined by the appended claims.

Meanwhile, the terms used in the specification are provided to only describe embodiments of the present invention and not for purposes of limitation. Unless the context clearly indicates otherwise, the singular forms include the plural forms. It will be understood that the terms "comprise" and/or "comprising," when used herein, specify some stated components, steps, operations and/or elements, but do not preclude the presence or addition of one or more other components, steps, operations and/or elements. The same reference number refers to the same component in the drawings throughout the specification, and the term "and/or" includes any and all combinations of one or more of the associated listed items. Although the terms "first," "second," etc. may be used to describe various elements, these elements should not be limited by these terms. These terms are only used to distinguish one element from another. Therefore, a first element could be termed a second element without departing from the scope of the present disclosure.

Unless otherwise defined, all terms (including technical and scientific terms) used herein can be used as is customary in the art to which this invention belongs. Also, it will be further understood that terms, such as those defined in commonly used dictionaries, will not be interpreted in an idealized or overly formal sense unless expressly so defined herein.

It will be further understood that the terms "comprise" and/or "comprising" used herein specify the presence of stated features or components, but do not preclude the presence or addition of one or more other features or components. Hereinafter, embodiments of the present invention will be described in detail with reference to the accompanying drawings.

Pulse energy, a pulse width, picoseconds, a laser wavelength, Q-switching, mode-locking, a single pulse, and cavity dumping are main factors of a skin treatment laser which is a technical field of the present disclosure. Since the terms are well known to those skilled in the art, detailed descriptions thereof will be omitted.

In addition, the present disclosure conforms to the contents described in Korean Registered Patent Publication No. 10-1682593 registered by the present applicant. Accordingly, the technical contents which are not described in the present disclosure can be referred to Korean Patent Publication No. 10-1682593.

FIG. 1 is a block diagram illustrating a single pulse laser apparatus according to one embodiment of the present disclosure.

Referring to FIG. 1, a single pulse laser apparatus 100 according to the present disclosure may include a first photodiode 111, a first synchronizer 112, a first delay unit 113, a second photodiode 121, a second synchronizer 122, a second delay unit 123, and a Q-driver 130. The single pulse laser apparatus 100 according to the present disclosure may further include a resonator 160. The resonator 160 may include a first mirror 161, a wave plate 162, an electro-optic modulator 163 configured to perform Q-switching, a gain medium 164, a linear polarizer 165, an etalon 166, an acousto-optic modulator 167 configured to perform mode-locking, and a second mirror 168.

Hereinafter, the first mirror 161, the wave plate 162, the electro-optic modulator 163 configured to perform Q-switching, the gain medium 164, the linear polarizer 165, the etalon 166, the acousto-optic modulator 167 configured to perform mode-locking, and the second mirror 168 which are included in the resonator 160 will be described first.

The first mirror 161 and the second mirror 168 may be disposed at both ends of the resonator 160. Each of the first mirror 161 and the second mirror 168 is a total reflector having a reflectivity of 99.9% or more in order to perform a cavity dumping method.

The wave plate 162 may control an intensity of a pulse generated in the resonator 160, and in one embodiment, a λ/4 plate may be used as the wave plate 162.

The gain medium 164 is a material of which a density may be inverted through pumping. A beam externally incident on the material is output as a beam of high intensity due to an amplification action of the material. A flash lamp, an arc lamp, or other lasers may be used as an external pumping device. A sapphire crystal rod doped with alexandrite or titanium or a yttrium-aluminum garnet crystal (Nd:YAG crystal) rod doped with neodymium may be used as the gain medium 164.

For example, when a beam is incident on the gain medium 164 using a pump lamp, the beam excited by the gain medium 164 passes through the etalon 166 along an optical axis 150 and is reflected by the second mirror 168. Then, the beam, which sequentially passes through the etalon 166, the gain medium 164, and the electro-optic modulator 163 along the optical axis 150, is reflected by the first mirror 161.

The linear polarizer 165 causes a laser beam oscillated in the resonator 160 to be output.

The acousto-optic modulator 167, which performs mode-locking, generates a mode-locking state and maximizes a cavity loss due to the wave plate 162 and the linear polarizer 165 to prevent oscillation and causes pumping energy to be stored in the gain medium 164.

The etalon 166 serves to adjust a pulse width of a laser beam, is formed as parallel flat plates having a predetermined reflectivity, and is an optical element generally formed by depositing a multilayered dielectric thin film on one side or both sides of the parallel flat plates formed of glass or quartz to increase the reflectivity. The etalon 166 was described in more detail with reference to FIG. 6 of Korean Patent Publication No. 10-1682593.

Hereinafter, the first photodiode 111, the first synchronizer 112, the first delay unit 113, the second photodiode 121, the second synchronizer 122, the second delay unit 123, the Q-driver 130, and the power supply 140 for generating a single pulse laser beam based on a laser beam oscillated by the resonator will be described.

The first photodiode 111 measures a laser beam oscillated by the resonator, generates an electrical signal for the measured laser beam, and inputs the electrical signal to the first synchronizer 112.

The first synchronizer 112 converts the electrical signal received from the first photodiode 111 into a transistor-transistor-logic (TTL) signal. Then, the first synchronizer 112 inputs the TTL signal to the first delay unit 113.

The first delay unit 113 outputs a trigger TTL signal, which is generated by setting a delay time to the TTL signal received from the first synchronizer 112, to the Q-driver 130.

The Q-driver 130 receives the trigger TTL signal, which is delayed by the specific delay time, from the first delay unit 113 and provides a voltage (V) to the electro-optic modulator 163 configured to perform Q-switching to cause the electro-optic modulator 163 to perform Q-switching.

Then, the second photodiode 121 measures a Q-switched pulse which is initially oscillated by the resonator and generates an electrical signal for the measured laser beam to input the electrical signal to the second synchronizer 122. The Q-switched pulse which is initially oscillated by the resonator means a laser beam generated due to a signal (hereinafter, a Q-switching pulse) generated to cause the Q-driver 130 to perform Q-switching.

The second synchronizer 122 converts the electrical signal, which is received from the second photodiode 121, to a TTL signal. Then, the second synchronizer 122 inputs the TTL signal to the second delay unit 123.

The second delay unit 123 outputs a trigger TTL signal, which is generated by setting a delay time to the TTL signal received from the first synchronizer 112, to the Q-driver 130. The delay time is a time for synchronizing Q-switched pulses and a cavity dumping timing.

According to one embodiment of the present disclosure, the first photodiode 111 may be positioned at a region adjacent to the first mirror 161 in the resonator 160, and the second photodiode 121 may be positioned at a region adjacent to the acousto-optic modulator 167 in the resonator 160. In addition, the photodiode 121 may be positioned adjacent to any region to which a Q-switched pulse may be scattered. The regions to which the Q-switched pulse may be scattered are regions adjacent to the first mirror 161, the wave plate 162, the electro-optic modulator 163, the gain medium 164, the linear polarizer 165, the etalon 166, and the second mirror 168, and the like.

In addition, although not illustrated in the drawing, the single pulse laser apparatus 100 according to the present disclosure may further include a controller configured to monitor a pulse width and pulse energy of a laser beam output from the resonator 160 to determine a delay time. For example, the controller may determine a delay time based on a time at which a pulse width of an output laser beam is smaller than a preset reference and pulse energy thereof is larger than a preset reference. The controller may provide the determined delay time to the first delay unit 113 and the second delay unit 123, and the first delay unit 113 and second delay unit 123 may set a corresponding delay time to a trigger TTL signal, delay the trigger TTL signal by the corresponding delay time, and provide the trigger TTL signal to the Q-driver 130. The delay time is determined by the controller to synchronize mode-locked and Q-switched pulses.

In addition, the controller may determine a duration time for which a trigger TTL signal lasts.

The single pulse laser apparatus 100 according to the present disclosure may further include a power supply 140 configured to supply energy to the gain medium and to input a synchronization TTL signal output when a lamp is pumped to the first delay unit and second delay unit. In addition, the lamp may be pumped using power supplied by the power supply 140, and a pumped beam may be incident on the gain medium 164 to supply energy necessary for generating a laser beam. In addition, the controller may determine a delay time on the basis of a relationship between an interval of prelased pulses and a width of a Q-switched pulse.

A signal flow will be described with reference to FIG. 1. The first photodiode 111 measures a laser beam oscillated by the resonator 160 and inputs an electrical signal to the first synchronizer 112. The first synchronizer 112 converts the electrical signal to a TTL signal and inputs the TTL signal to the first delay unit 113. The first delay unit 113 generates a trigger TTL signal after being delayed by a preset delay time and inputs the trigger TTL signal to the Q-driver 130. When the trigger TTL signal is generated after being delayed by the preset delay time, a mode-locked pulse may be accurately synchronized with a Q-switched pulse so that the Q-switched pulse may be output.

Then, the second photodiode 121 measures a Q-switched pulse of a laser beam which is generated due to the Q-switching pulse and initially oscillated by the resonator and inputs an electrical signal to the second synchronizer 122. The second synchronizer 122 converts the electrical signal to a TTL signal and inputs the TTL signal to the second delay unit 123. The second delay unit 123 generates a trigger TTL signal after delaying the trigger TTL by a preset delay time and inputs the trigger TTL signal to the Q-driver 130. Finally, since the signal output from the second delay unit is a trigger signal that always follows the Q-switching pulse, a pulse occurring at an arbitrary time may be actively substituted. That is, a trigger signal different from a trigger signal output from the first delay unit 113 is input to the Q-driver 130 to cavity dumping to occur. The trigger signal generated by the second delay unit 123 may cause the cavity dumping to occur when energy of the Q-switching pulse is the highest. Accordingly, the energy of a single pulse can be increased and the safety of output can be improved.

Meanwhile, each of the first delay unit 113 and the second delay unit 123 may receive a synchronization TTL signal output from the power supply 140 when the power supply 140 pumps the lamp and input a trigger TTL signal to the Q-driver 130.

The Q-driver 130 may be driven by receiving the trigger TTL signal and operate the electro-optic modulator 163 configured to perform Q-switching.

Figure 2:
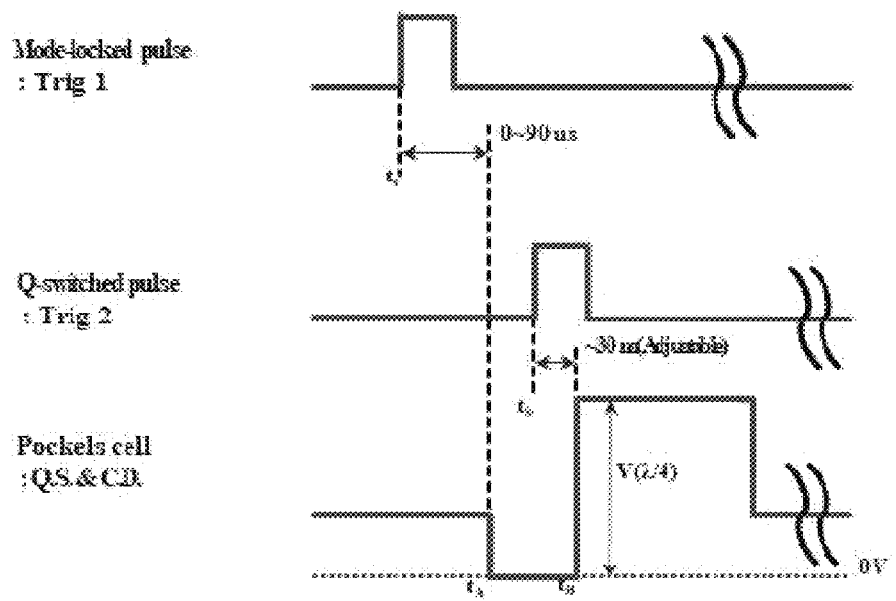
FIG. 2 is a graph illustrating a process of performing Q-switching according to a trigger transistor-transistor-logic (TTL) signal according to the present disclosure.
Figure 2:
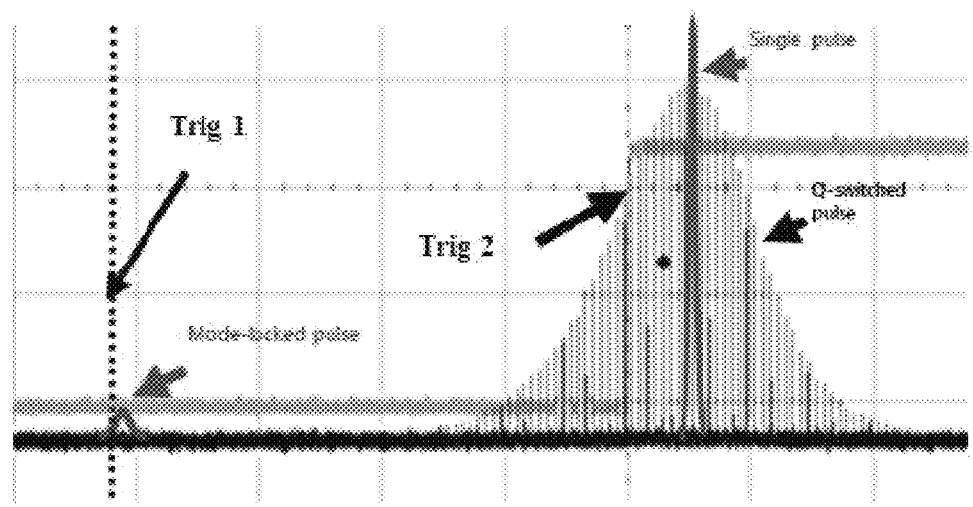

FIG. 2 is a graph illustrating a process of performing Q-switching according to a TTL signal according to the present disclosure.

An upper drawing in FIG. 2 shows temporal points at which Q-switching and cavity dumping occur according to a trigger TTL signal according to the present disclosure. A laser beam oscillated by the resonator is measured by the first photodiode 111 and is input to the first synchronizer 112. Then, a signal $t_a$ of Trig 1 is generated and input to the first delay unit 113 to determine a Q-switching timing $t_A$ after delaying the signal $t_a$ by an appropriate time. A laser beam of a Q-switched pulse which is oscillated later is measured by the second photodiode 121 and is input to the second synchronizer 122. An appropriate timing delay is applied to Trig 2 generated through above-described process by the second delay unit 123 to determine a cavity dumping timing $t_B$.

A lower graph of FIG. 2 shows a Q-switched pulse generated at the timing $t_A$ determined by Trig 1 described above. The Q-switched pulse is arbitrarily indicated with a red line to simultaneously represent a single pulse which will be generated at the cavity dumping timing $t_B$ determined by Trig 2. Therefore, it can be understood that the cavity dumping timing $t_B$ may always be determined at a peak point of the Q-switched pulse because Trig 2 always follows the Q-switched pulse.

On the other hand, in a conventional method, since a cavity dumping timing is determined after delaying by a certain time delay from Trig 1, when a peak of a Q-switched pulse is not always at the same point in time, efficiency of cavity dumping decreases, output energy of a single pulse also decreases, and thus stability of the energy is also lowered. The lower graph of FIG. 2 is attached to illustrate this comparison. In the graph of FIG. 2, since the Q-switched pulse is not always present in the same position in time, a peak point is not always present at the same point in time.

The single pulse laser apparatus 100 according to the present disclosure may further include the etalon 166 configured to adjust a pulse width of a laser beam in a range of 100 ps to 1 ns. The etalon 166 is formed as parallel flat plates having a predetermined reflectivity and is an optical element formed by depositing a multilayered dielectric film on one side or both sides of the parallel flat plates formed of glass or quartz to increase the reflectivity. Accordingly, when a laser beam passes through the etalon, a wavelength band may be limited so that a pulse width of the laser beam can be adjusted due to the reflectivity, thickness, and refractive index of the etalon.

A pulse width of a Q-switched and mode-locked pulse which is output after prelasing may be adjusted to a pulse width of 1 ns or more using the etalon 166, and the etalon 166 having various thicknesses may be used to adjust a pulse width. More specifically, when a laser beam passes through the etalon 166, a transmission wavelength band of the laser beam is limited according to the reflectivity, thickness, and refractive index of the etalon 166, and thus a pulse width is adjusted.

By adjusting the number of etalons 166, a degree of freedom may be increased for adjusting a pulse width of a laser beam. In addition, one or more etalons 166 may be provided, and etalons having different characteristics may be selectively used inside or outside the resonator such that a pulse width of a laser beam may be adjusted. For example, for medical lasers, it is preferable that a width of a laser pulse be freely adjusted in a range of 100 ps to 1 ns.

In a case in which the etalon 166 is disposed outside the resonator 160 (in the case of an extra-cavity), since a laser beam passes through the etalon 166 only once while being output, a reflectivity thereof has to be very high to achieve an effect of forming a desired pulse width. On the other hand, in a case in which the etalon 166 is installed inside the resonator 160 (in the case of an intra-cavity), even when the etalon 166, which does not include a dielectric thin film, has a low reflectivity of about 4% and is formed in a simple flat plate type, since a laser beam sufficiently reciprocates in the resonator 160, the same effect as that of an etalon which is installed outside the resonator 160 and having a high reflectivity can be achieved. Accordingly, there is an advantage of selecting an appropriate pulse width for treatment.

Experimental Example

In order to verify an effect of the single pulse laser apparatus according to the present disclosure, a comparative experiment between the single pulse laser apparatus and a conventional single pulse laser apparatus was conducted.

Figure 3:
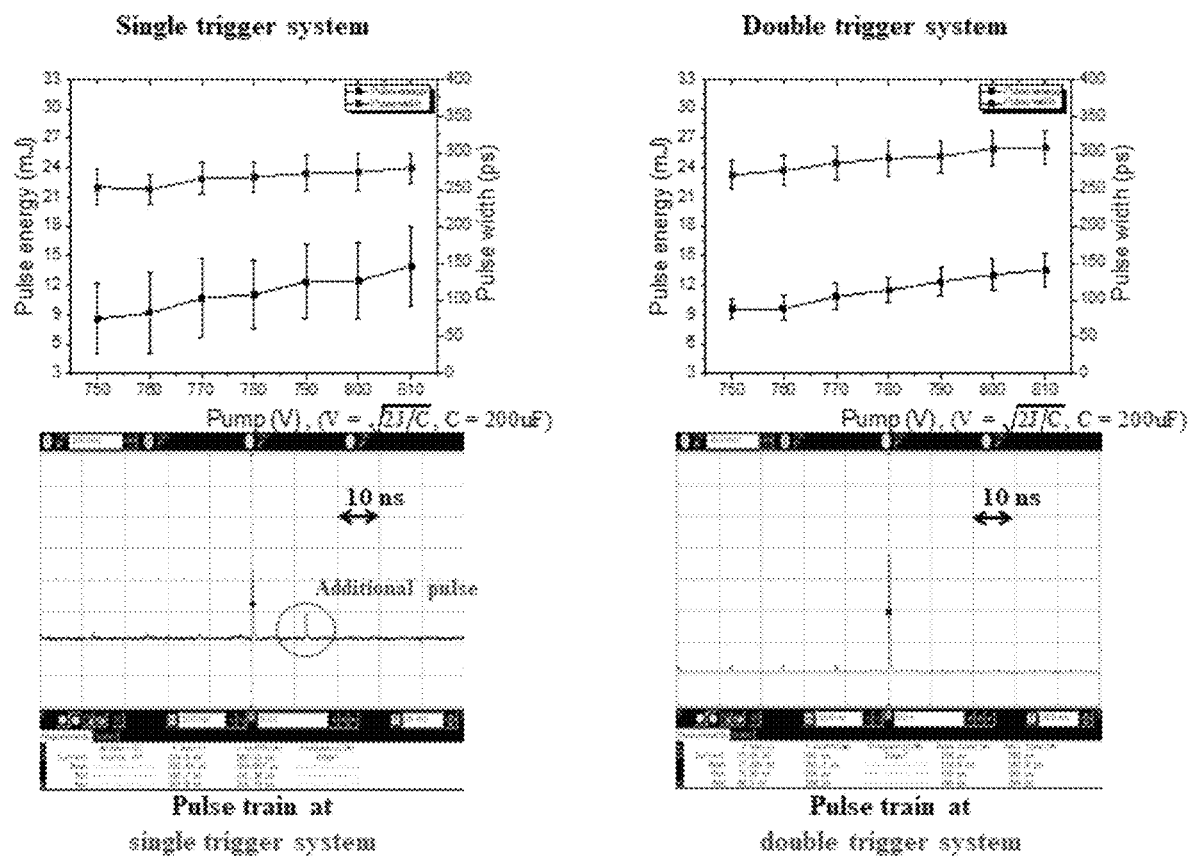
FIG. 3 is a graph of a comparative experimental result.

FIG. 3 is a graph of a comparative experimental result.

Referring to FIG. 3, it can be seen that stability of single pulse energy output by the single pulse laser apparatus using double trigger according to the present disclosure was improved as compared to that output by a conventional single pulse laser apparatus using single trigger. In addition, it can be seen that multiple pulses which were irregularly generated were suppressed. It can also be seen that the single pulse energy was improved through the suppression of the multiple pulses.

As described above, according to one aspect of the present disclosure, a single pulse laser apparatus can calculate a correlation between a pulse width of a Q-switched signal and mode-locked signals and reflects the correlation in a laser system so that a single pulse can be output, an energy can be concentrated on a laser beam configured to output a single pulse through a cavity dumping technology, and a continuous wave (CW) mode-locked signal can be reflected in an output beam with a picosecond pulse width through a prelasing method.

According to another aspect of the present disclosure, additional pulses can be suppressed through double trigger, single pulse energy can be increased, and stability of an output can be improved.

According to still another aspect of the present disclosure, a Q-switched output of a cavity dumping laser can be stabilized and additional pulse oscillation can be suppressed through a double trigger method so that the single pulse energy can be increased.

Effects of the present invention are not limited to the above-described effect, and other effects which are not described above may be clearly understood by those skilled in the art from the above detailed description.

While the embodiments of the present disclosure have been described with reference to the accompanying drawings, it will be understood by those skilled in the art that the invention may be performed in other concrete forms without changing the technological scope and essential features. Therefore, the above-described examples should be considered in a descriptive sense only and not for purposes of limitation.

What is claimed is:

1. A single pulse laser apparatus including a resonator which has a first mirror, a second mirror, a gain medium, an electro-optic modulator and an acousto-optic modulator configured to respectively perform Q-switching and mode-locking, the single pulse laser apparatus comprising:
    a first photodiode configured to measure a laser beam oscillated and output by the resonator;
    a first synchronizer configured to convert an electrical signal output from the first photodiode to a first transistor-transistor-logic (TTL) signal and output the first TTL signal;
    a first delay unit configured to set a first delay time which is determined in order to synchronize mode-locked and Q-switched pulses with the first TTL signal output from the first synchronizer, and output a first trigger TTL signal according to the first delay time;
    a second photodiode configured to measure a Q-switched pulse initially oscillated by the resonator;
    a second synchronizer configured to convert an electrical signal output from the second photodiode to a second TTL signal and output the second TTL signal;
    a second delay unit configured to set a second delay time which is determined in order to synchronize Q-switched pulses and a cavity dumping timing with the second TTL signal output from the second synchronizer, and output a second trigger TTL signal according to the second delay time; and
    a Q-driver configured to input the first trigger TTL signal and the second trigger TTL signal to the electro-optic modulator configured to perform the Q-switching to operate the electro-optic modulator.

2. The single pulse laser apparatus of claim 1, wherein:
    the first photodiode is positioned at a region adjacent to the first mirror in the resonator; and
    the second photodiode is positioned at a region adjacent to the acousto-optic modulator in the resonator.

3. The single pulse laser apparatus of claim 1, further comprising a controller configured to monitor a pulse width and pulse energy of the laser beam output by the resonator, and determine at least one of the first delay time or the second delay time.

4. The single pulse laser apparatus of claim 3, wherein the controller determines a duration time for which at least one of the first trigger TTL signal or the second trigger TTL signal lasts.

5. The single pulse laser apparatus of claim 1, further comprising a power supply configured to supply energy to the gain medium and input a synchronization TTL signal, which is output when a lamp is pumped, to the first delay unit and the second delay unit.

6. The single pulse laser apparatus of claim 3, wherein the acousto-optic modulator configured to perform the mode-locking prelases pulses of laser beams having specific picosecond pulse widths.

7. The single pulse laser apparatus of claim 6, wherein the controller determines at least one of the first delay time or the second delay time on a basis of a relationship between an interval of the prelased pulses and a pulse width of the Q-switched pulse.

8. The single pulse laser apparatus of claim 1, further comprising an etalon configured to adjust a pulse width of the laser beam to be in a range of 100 ps to 1 ns.

9. The single pulse laser apparatus of claim 8, wherein the etalon is formed as parallel flat plates having a predetermined reflectivity, is an optical element formed by depositing a multilayered dielectric thin film on one side or both sides of the parallel flat plates, the parallel flat plates being formed of glass or quartz to increase the reflectivity, and limits a transmission wavelength band when the laser beam passes through the etalon so that the pulse width of the laser beam is adjusted due to the reflectivity, a thickness, and a refractive index of the etalon.

10. The single pulse laser apparatus of claim 8, wherein the etalon includes one or more etalons, the etalons have different characteristics, and the etalons are selectively used inside or outside the resonator to adjust the pulse width of the laser beam.

* * * * *